United States Patent [19]
Schroeder, deceased et al.

[11] 4,411,910
[45] Oct. 25, 1983

[54] BENZOFURAN DERIVATIVES AND THEIR PHARMACEUTICAL USE

[75] Inventors: Eberhard Schroeder, deceased, late of Berlin, Fed. Rep. of Germany, by Kirsten Schroeder, Christian Schroeder, legal representatives; Manfred Lehman; Clemens Rufer, both of Berlin, Fed. Rep. of Germany

[73] Assignee: Schering Aktiengesellschaft, Berlin and Bergkamen, Fed. Rep. of Germany

[21] Appl. No.: 357,344

[22] Filed: Mar. 11, 1982

[30] Foreign Application Priority Data
Mar. 11, 1981 [DE] Fed. Rep. of Germany ....... 3110009

[51] Int. Cl.³ .................. A61K 31/34; A61K 31/365; C07D 307/79; C07D 307/88
[52] U.S. Cl. .................................... 424/279; 424/285; 549/304; 549/466; 549/467
[58] Field of Search ...................... 549/304, 466, 467; 424/279, 285

[56] References Cited
U.S. PATENT DOCUMENTS
4,367,238  1/1983  Ueda et al. .......................... 424/279

Primary Examiner—Henry R. Jiles
Assistant Examiner—Bernard Dentz
Attorney, Agent, or Firm—Millen & White

[57] ABSTRACT

Benzofuran derivatives of the formula

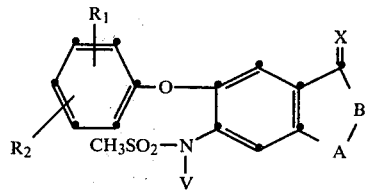

wherein
V is hydrogen or acetyl,
X is oxo or two hydrogen atoms,
$R_1$ and $R_2$ each independently is hydrogen, fluorine, or chlorine, and
—A—B— is —O—$CH_2$— or —$CH_2$—O—,
possess valuable pharmacological properties.

18 Claims, No Drawings

BENZOFURAN DERIVATIVES AND THEIR PHARMACEUTICAL USE

This invention relates to new benzofuran derivatives, their preparation and use.

SUMMARY OF THE INVENTION

It is an object of this invention to provide new medicinal compounds.

Upon further study of the specification and appended claims, further objects and advantages of this invention will become apparent to those skilled in the art.

These objects of this invention have been attained by providing benzofuran derivatives of formula I

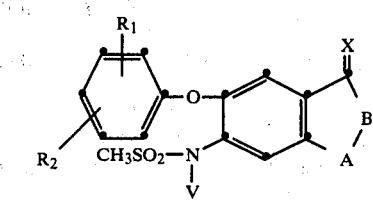

wherein

V is hydrogen or acetyl,

X is oxo or two hydrogen atoms, $R_1$ and $R_2$ each independently is hydrogen, fluorine, or chlorine, and —A—B— is —O—CH$_2$— or —CH$_2$—O—.

DETAILED DISCUSSION

The substituents $R_1$ and $R_2$ of the benzofuran derivatives can be identical or different and can be in any position or combination of positions, e.g., o, p-difluoro.

The novel benzofuran derivatives of this invention can be produced according to methods known per se. Suitable preparation processes include a process for preparing benzofuran derivatives of formula (I) comprising, in conventional manner, (a) condensing a compound of formula II

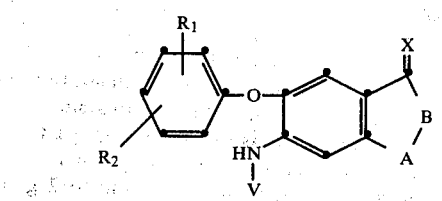

wherein $R_1$, $R_2$, X, V, and —A—B— are as defined above, with methanesulfonic acid chloride or anhydride, and, optionally, conventionally acetylating the resultant benzofuran derivatives of formula I wherein V is hydrogen; or (b) to prepare benzofuran derivatives of formula I wherein —A—B— is —O—CH$_2$— and X is oxo, cyclizing a compound of formula III

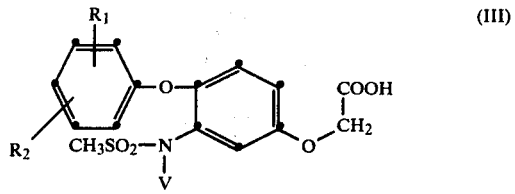

wherein $R_1$, $R_2$, and V are as defined above, and, optionally, conventionally acetylating the resultant benzofuran derivatives wherein V is hydrogen.

The condensation of the compounds of formula II with methanesulfonic acid chloride or anhydride takes place under conventional conditions, for example, by reacting the sulfonic acid chlorides in the presence of alkaline catalysts, such as sodium carbonate, sodium hydroxide, potassium bicarbonate, potassium carbonate, pyridine, lutidine, or collidine, with the compounds of formula II. Such conventional reactions are exemplified below.

The cyclization of the phenoxyacetic acids of formula III to obtain the corresponding 3-benzofuranones takes place, for example, with strong acids effective for splitting off water, for example by heating in toluene with p-toluenesulfonic acid or in polyphosphoric acid, or by reaction, for example, with thionyl chloride, phosphorus pentachloride, etc. to form the corresponding phenoxy-acetic acid chlorides and then Friedel-Crafts reaction of the latter in the presence of appropriate catalysts, such as aluminum chloride, etc. These conventional reactions are also exemplified below.

The starting compounds for the condensation process of this invention are conventional or can be prepared using conventional methods. Thus, it is possible, for example, to prepare the compounds of formula II by conventional condensation of compounds of formula IV with compounds of formula V and subsequent conventional reduction of the resultant nitro compounds of formula VI. (In these formulae, $R_1$, $R_2$, X and —A—B— are as defined above and Y is chlorine, bromine, or iodine). The compounds of formula V are conventional or can be conventionally prepared as illustrated below. All other reactions are also fully conventional and can be carried out as illustrated below.

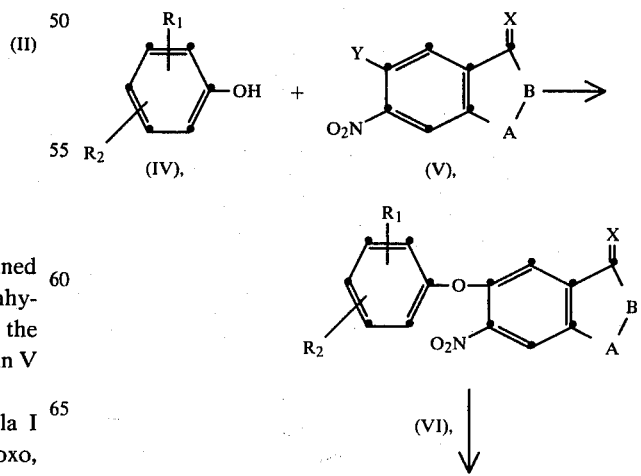

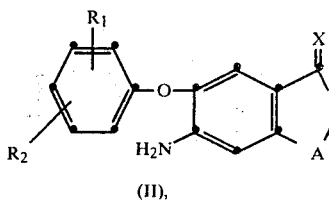

(II),

The compounds of formula III can be produced by conventional condensation of the compounds of formula IV with 4-chloro-3-nitroanisole VII, conventional cleavage of the methyl ether to obtain the compound of formula IX, conventional condensation with ethyl bromoacetate to obtain the compound of formula X, conventional reduction of the nitro group to obtain the compound of formula XI, conventional mesylation of the amino group to form the compound of formula XII, and conventional saponification of the ester group: (In these formulae, the substituents $R_1$ and $R_2$ likewise are as defined above.)

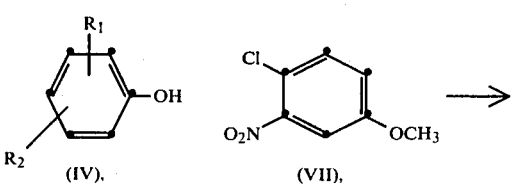

(IV),   (VII),

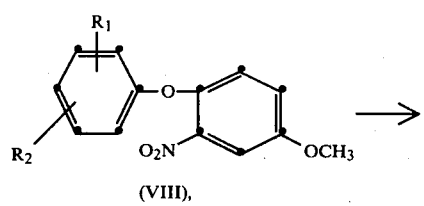

(VIII),

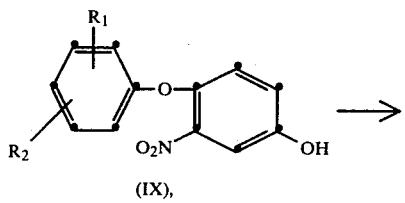

(IX),

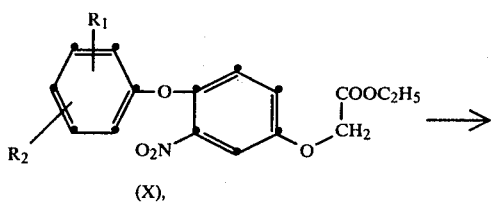

(X),

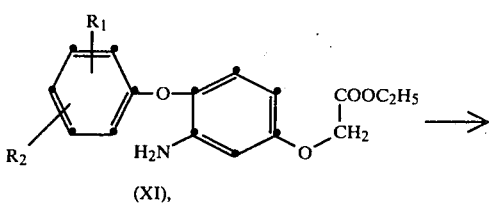

(XI),

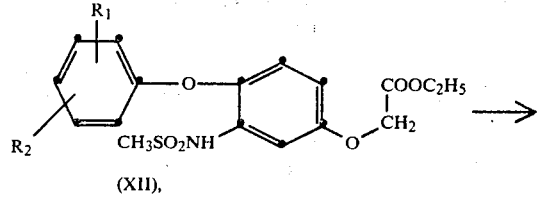

(XII), (III)

Again, all of these reactions are conventional and can be carried out as illustrated below.

The compounds of this invention are distinguished by a good antiphlogistic activity.

Moreover, the compounds of this invention excel in their analgesic, antidysmenorrheic, antipyretic, thrombocyte-aggregation-inhibiting, and diuretic effectiveness. It is moreover remarkable that these compounds hardly inhibit prostaglandin synthesis at all. A special advantage of these compounds is their high dissociation between therapeutic activity and undesirable side effects, particularly, ulcerogenesis.

Accordingly, all of these novel compounds, in combination with the excipients customary in galenic pharmacy, are suitable for the treatment of diseases of the rheumatoid-type spectrum, (such as rheumatoid arthritis, osteoarthritis, or ankylosing spondylitis), bronchial asthma, hay fever, and others. It is furthermore remarkable that the benzofuran derivatives of this invention are additionally suitable for the treatment of migraine and dysmenorrhea, and reduce the risk of thrombosis.

Typically, the compounds of this invention are administered to mammals, including humans, in dosages of 0,2–2,0 mg/kg/day for these uses. Such administration is fully analogous to the conventional agent indometacine as an antiinflammatory Among the benzofuran derivatives of this invention, surprisingly, are also those which, in addition, possess a pronounced antiulcerogenic as well as tumor-inhibiting activity.

The medical specialties of this invention are produced as usual by converting the active agents, together with suitable additives, vehicles, and flavor-ameliorating agents, into the desired forms of administration such as tablets, dragees, capsules, solutions, inhalants, etc.

Suitable for oral administration are, in particular, tablets, dragees, and capsules containing, for example, 1–250 mg of active ingredient and 50 mg to 2 g of a pharmacologically inert excipient, as well as the usual additives. Conventional excipients for use in the pharmaceutical compositions of this invention are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host can be determined, using conventional considerations, e.g., by customary comparison of the differential activities of the subject compound and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

(a) 9.5 g of 2,3-dihydrobenzo[b]furan-5-amine in 40 ml of acetic acid and 10 ml of acetic anhydride is heated to 60° C. for 1½ hours and concentrated. The residue is recrystallized from aqueous ethanol. Yield: 11.5 g of N-(2,3-dihydrobenzo[b]furan-5-yl)acetamide, mp 96° C.

(b) Under ice cooling, 440 g of N-(2,3-dihydrobenzo[b]furan-5-yl)acetamide in 4 l of acetic acid is combined within 30 minutes with 210 ml of nitric acid (65% strength) and stirred for 2 hours. The mixture is diluted with water, the crystallized product is vacuum-filtered and washed with water. Yield: 515 g of N-(6-nitro-2,3-dihydrobenzo[b]furan-5-yl)acetamide, mp 141°–142° C.

(c) 89 g of N-(6-nitro-2,3-dihydrobenzo[b]furan-5-yl)acetamide in 1 l of ethanol and 400 ml of hydrochloric acid is refluxed for 2 hours and concentrated. The residue is combined with 2 N sodium hydroxide solution/ethyl acetate, the aqueous phase is again extracted once with ethyl acetate, and the combined organic phases are concentrated, thus obtaining from ethyl acetate 66 g of 6-nitro-2,3-dihydrobenzo[b]furan-5-amine, mp 152° C.

(d) 54 g of 6-nitro-2,3-dihydrobenzo[b]furan-5-amine in 100 ml of acetic acid and 150 ml of water is combined at 5° C. with 50 ml of sulfuric acid, reacted within 30 minutes at −5° to 0° C. with 21 g of sodium nitrite in 50 ml of water, and stirred for 30 minutes (solution 1).

150 g of copper(II) sulfate and 93 g of sodium bromide are dissolved under heating in 800 ml of water and combined within 15 minutes with 39 g of sodium sulfite. The thus-precipitated copper(I) bromide is vacuum-filtered and dissolved in 750 ml of 16% hydrobromic acid (solution 2).

Solution 1 is added dropwise to solution 2 within 15 minutes at 90° C. (bath temperature 110° C.) and stirred for 10 minutes at 90° C. The mixture is cooled, the precipitate vacuum-filtered, washed with 2 N hydrochloric acid and water, and recrystallized from ethanol. Yield: 68.5 g of 5-bromo-6-nitro-2,3-dihydrobenzo[b]furan, mp 103° C.

(e) 2.95 g of 5-bromo-6-nitro-2,3-dihydrobenzo[b]furan, 5.6 g of phenol, 5 g of potassium carbonate, and 300 mg of copper(I) chloride are refluxed in 60 ml of absolute pyridine for 2 hours under nitrogen. After concentration, the residue is taken up in ethyl acetate/1 N hydrochloric acid, extracted twice with 1 N hydrochloric acid and three times with 1 N sodium hydroxide solution, the organic phase is dried, concentrated, and recrystallized twice from diisopropyl ether. Yield: 2 g of 6-nitro-5-phenoxy-2,3-dihydrobenzo[b]furan, mp 94°–94.5° C.

(f) 2.3 g of 6-nitro-5-phenoxy-2,3-dihydrobenzo[b]furan in 90 ml of methanol is hydrogenated for 4 hours in the presence of 2 g of Raney nickel at 70 bar, vacuum-filtered from the catalyst, concentrated, and recrystallized from methanol. Yield: 1.7 g of 5-phenoxy-2,3-dihydrobenzo[b]furan-6-amine, mp 130°–131° C.

(g) 1.15 g of 5-phenoxy-2,3-dihydrobenzo[b]-furan-6-amine in 10 ml of pyridine is combined at 0° C. with 0.52 ml of methanesulfonyl chloride. After 3 hours at 0° C. and 13 hours at 20° C., the mixture is concentrated, the residue is taken up in chloroform, the solution is washed three times with 1 N hydrochloric acid and concentrated.

After recrystallization of the residue from ethanol, 1.2 g of N-(5-phenoxy-2,3-dihydrobenzo[b]furan-6-yl)methanesulfonamide is obtained, mp 133° C.

EXAMPLE 2

(a) 4.8 g of 5-bromo-6-nitro-2,3-dihydrobenzo[b]furan, 3.4 g of 2-fluorophenol, 2 g of copper(I) chloride, and 3.4 g of potassium tert-butanolate are refluxed in 70 ml of tert-butanol for 5½ hours. The mixture is concentrated, the residue taken up in ethyl acetate/2 N hydrochloric acid, the organic phase washed three times with 2 N hydrochloric acid and three times with 2 N sodium hydroxide solution, concentrated, and the residue chromatographed over a silica gel column with toluene.

Yield: 0.9 g of 5-(2-fluorophenoxy)-6-nitro-2,3-dihydrobenzo[b]furan as an oil and 0.9 g of 5-(2-fluorophenoxy)-6-nitrobenzo[b]furan, mp 91° C. (from diisopropyl ether).

(b) 550 mg of 5-(2-fluorophenoxy)-6-nitrobenzo[b]furan in 50 ml of methanol is hydrogenated within 6 hours at 70 bar in the presence of 500 mg of Raney nickel, filtered, and recrystallized from ethanol. Yield: 390 mg of 5-(2-fluorophenoxy)-2,3-dihydrobenzo[b]furan-6-amine, mp 105°–106.5° C.

(c) 370 mg of 5-(2-fluorophenoxy)-2,3-dihydrobenzo[b]furan-6-amine in 4 ml of pyridine is reacted with 0.16 ml of methanesulfonyl chloride, as described in Example 1(g).

Yield: 395 mg of N-[5-(2-fluorophenoxy)-2,3-dihydrobenzo[b]furan-6-yl]methanesulfonamide, mp 111°–112° C. (from ethanol).

EXAMPLE 3

(a) 24 g of 5-bromo-6-nitro-2,3-dihydrobenzo[b]-furan, 20 g of 2,4-difluorophenol, 10 g of copper(I) chloride, and 17 g of potassium tert-butanolate in 350 ml of tert-butanol are refluxed for 4 hours, concentrated, and the residue taken up in ethyl acetate/2 N hydrochloric acid. The mixture is extracted three times with 1 N hydrochloric acid and four times with 1 N sodium hydroxide solution, the ethyl acetate phase is concentrated, and the crude product is purified on a silica gel column (system: toluene). Yield: 3.8 g of 5-(2,4-difluorophenoxy)-6-nitrobenzo[b]-furan, mp 88°–89° C. (from diisopropyl ether) and 15 g of 5-(2,4-difluorophenoxy)-6-nitro-2,3-dihydrobenzo[b]furan as an oil.

(b) Method A 2.9 g of 5-(2,4-difluorophenoxy)-6-nitrobenzo[b]furan in 100 ml of methanol is hydrogenated in the presence of 3 g of Raney nickel within 6 hours at 70 bar. The product is removed from the catalyst by vacuum-filtering, concentrated, and recrystallized from ethanol. Yield: 2.4 g of 5-(2,4-difluorophenoxy)-2,3-dihydrobenzo[b]furan-6-amine, mp 74°–75° C.

Method B 18 g of 5-(2,4-difluorophenoxy)-6-nitro-2,3-dihydrobenzo[b]furan in 500 ml of methanol is hydrogenated and recrystallized as described in Example 3(b), Method A. Yield: 5 g of 5-(2,4-difluorophenoxy)-2,3-dihydrobenzo[b]furan-6-amine, mp 70°–72.5° C.

(c) 2.1 g of 5-(2,4-difluorophenoxy)-2,3-dihydrobenzo[b]furan-6-amine, 0.8 ml of methanesulfonyl chloride in 40 ml of pyridine are stirred for 2 hours at 0° C. and for 14 hours at room temperature and concentrated. The crude product is dissolved in chloroform, washed three times with 1 N hydrochloric acid, again concentrated, and recrystallized twice from ethanol. Yield: 2.55 g of N-[5-(2,4-difluorophenoxy)-2,3-dihydrobenzo[b]furan-6-yl]-methanesulfonamide, mp 111.5° C.

EXAMPLE 4

(a) 3.6 g of 5-bromo-6-nitro-2,3-dihydrobenzo[b]-furan, 4.4 g of 2-chloro-4-fluorophenol, 3.3 g of potassium tert-butanolate, 1.5 g of copper(I) chloride are reacted as described in Example 2(a). After purifying on a silica gel column (system: toluene), 0.7 g of 5-(2-chloro-4-fluorophenoxy)-6-nitrobenzo[b]furan, mp 103.5° to 105° C. (from diisopropyl ether) and 2.7 g of crude 5-(2-chloro-4-fluorophenoxy)-6-nitro-2,3-dihydrobenzo[b]furan (after repeated crystallization from methanol/water, mp 86°–88° C.) are obtained.

(b) 2.7 g of crude 5-(2-chloro-4-fluorophenoxy)-6-nitro-2,3-dihydrobenzo[b]furan is hydrogenated as set forth in Example 1(f) and recrystallized from aqueous ethanol. Yield: 1.8 g of 5-(2-chloro-4-fluorophenoxy)-2,3-dihydrobenzo[b]furan-6-amine, mp 106°–108° C.

(c) Analogously to Example 1(g), 800 mg of 5-(2-chloro-4-fluorophenoxy)-2,3-dihydrobenzo[b]furan-6-amine yields 800 mg of N-[5-(2-chloro-4-fluorophenoxy)-2,3-dihydrobenzo[b]furan-6-yl]methanesulfonamide, mp 156°–157° C.

EXAMPLE 5

Under ice cooling, 1.7 g of N-[5-(2,4-difluorophenoxy)-2,3-dihydrobenzo[b]furan-6-yl]methanesulfonamide in 15 ml of pyridine is combined with 0.85 ml of acetic anhydride, stirred for 3 hours at 0° C. and for 13 hours at room temperature, then concentrated, and the residue is dissolved in chloroform, washed three times with 1 N hydrochloric acid, concentrated, and twice recrystallized from ethanol.

Yield: 1.65 g of N-acetyl-N-[5-(2,4-difluorophenoxy)-2,3-dihydrobenzo[b]furan-6-yl]methanesulfonamide, mp 151.5°–153° C.

EXAMPLE 6

(a) 37.5 g of 4-chloro-3-nitroanisole, 94 g of phenol, 5 g of copper(I) chloride, and 69 g of potassium carbonate in 400 ml of pyridine are refluxed for 6 hours, concentrated, the residue taken up in ethyl acetate/1 N hydrochloric acid, the organic phase washed three times with 1 N hydrochloric acid and three times with 1 N sodium hydroxide solution, dried, and concentrated. The residue is distillated under vacuum (bp 0.04 mm Hg 143°–146° C.) and recrystallized from hexane. Yield: 24.5 g of (4-methoxy-2-nitrophenyl)phenyl ether, mp 33°–34° C.

(b) 24.5 g of (4-methoxy-2-nitrophenyl)phenyl ether in 150 ml of acetic acid, 100 ml of acetic anhydride are combined with 200 ml of hydrobromic acid (48% strength) and refluxed for 3½ hours and partially concentrated. The mixture is combined with ice water and extracted once with ethyl acetate. The organic phase is washed four times with water and recrystallized twice from diisopropyl ether. Yield: 20 g of 3-nitro-4-phenoxyphenol, mp 101°–102.5° C.

(c) 2.3 g of 3-nitro-4-phenoxyphenol in 20 ml of absolute dimethylformamide is agitated at 0° C. with 360 mg of sodium hydride (80%) for 15 minutes and combined with 1.4 ml of ethyl 2-bromoacetate. After 3 hours at room temperature, the mixture is concentrated, the residue is taken up in ethyl acetate/1 N sodium hydroxide solution, and the organic phase is washed three times with 1 N sodium hydroxide solution and twice with water. Yield: 2.9 g of 2-(3-nitro-4-phenoxyphenoxy)acetic acid ethyl ester as an oil.

(d) 10.5 g of 2-(3-nitro-4-phenoxyphenoxy)acetic acid ethyl ester in 500 ml of ethanol is hydrogenated in the presence of 10 g of Raney nickel in 4 hours at 70 bar, filtered, concentrated, and recrystallized from ethanol. Yield: 9 g of 2-(3-amino-4-phenoxyphenoxy)acetic acid ethyl ester, mp 87°–88° C.

(e) 5.7 g of 2-(3-amino-4-phenoxyphenoxy)acetic acid ethyl ester in 50 ml of pyridine is reacted with 2 ml of methanesulfonyl chloride as described in Example 1(g). Yield: 6.3 g of 2-(3-mesylamino-4-phenoxyphenoxy)acetic acid ethyl ester, mp 84° C. (from ethanol).

(f) 5.8 g of 2-(3-mesylamino-4-phenoxyphenoxy)acetic acid ethyl ester in 160 ml of methanol and 24 ml of 2 N sodium hydroxide solution are stirred for 2½ hours at room temperature, partially concentrated, combined with ice water, and acidified with 1 N hydrochloric acid. The precipitate is dissolved in ethyl acetate, the organic phase is washed twice with water, concentrated, and the residue is recrystallized from ethyl acetate/hexane. Yield: 5.2 g of 2-(3-mesylamino-4-phenoxyphenoxy)acetic acid, mp 135°–136° C.

(g) 3.75 g of 2-(3-mesylamino-4-phenoxyphenoxy)acetic acid in 15 ml of thionyl chloride is refluxed for 5 minutes and stirred for 30 minutes at room temperature. The mixture is concentrated, the residue dissolved three times in 1,2-dichloroethane, and the solvent removed by distillation.

The crude acid chloride is dissolved in 20 ml of 1,2-dichloroethane, added dropwise within 30 minutes at −5° C. to 20 ml of 1,2-dichloroethane and 2.4 g of aluminum chloride, agitated for 1 hour at −5° C., and the batch is poured on ice water. The organic phase is separated, dried, concentrated, and the residue purified on a silica gel column (system: cyclohexane/ethyl acetate 1.5+1).

Yield: 1.08 g of N-(3-oxo-5-phenoxy-2,3-dihydrobenzo[b]furan-6-yl)methanesulfonamide, mp 163.5°–164.5° C.

EXAMPLE 7

(a) 46 g of copper(II) sulfate.5 H$_2$O and 26.9 g of sodium bromide are dissolved in 160 ml of water at 40° C. and 13.3 g of sodium sulfite is added thereto (decolorization). After cooling to 0° C., the mixture is vacuum-filtered, the precipitate taken up in 160 ml of water, and 13.2 g of sodium bromide as well as 66 ml of 48% hydrobromic acid are added thereto. After heating to 70° C., a clear solution is produced (solution 1). At 20°–25° C., a solution of 23.5 g of 2-nitro-4,5-dimethylaniline in acetic acid (470 ml) warmed to 30°–40° C. is added dropwise to a solution of 10 g of sodium nitrite in 132 g of concentrated sulfuric acid (solution 2). Solution 2 is then gradually added dropwise under agitation to solution 1, heated to 70° C. After 1 hour of additional agitation at 70° C., the mixture is cooled, poured on 2 l of ice water, vacuum-filtered, and recrystallized from ethanol. Yield: 21.3 g of 2-bromo-4,5-dimethylnitrobenzene, mp 60° C.

(b) 23 g of 2-bromo-4,5-dimethylnitrobenzene, 22.4 g of potassium tert-butanolate, 20.6 g of phenol, and 4 g of copper(I) chloride are refluxed in 500 ml of tert-butanol for 2½ hours. After cooling and concentration, the mixture is combined with 700 ml of ether and filtered over kieselguhr. The filtrate is washed with 1 N sodium hydroxide solution, concentrated, and the residue distilled under vacuum. Yield: 14.1 g of 4,5-dimethyl-2-nitrophenoxybenzene, bp 0.17 mm Hg 156°–157° C.

(c) At 80°–90° C., 20 g of 4,5-dimethyl-2-nitrophenoxybenzene in 80 ml of pyridine and 320 ml of water is combined within 1½ hours with 207 g of potassium permanganate and stirred for 6 hours at 90° C. The mixture is combined with 500 ml of water, vacuum-filtered, washed thoroughly with water, and the mother liquor acidified under ice cooling with 5 N sulfuric acid. The precipitate is vacuum-filtered, dried, and recrystallized from ethyl acetate. Yield: 13.9 g of 4-nitro-5-phenoxyphthalic acid, mp 164° C.

(d) Under nitrogen, 9 g of 4-nitro-5-phenoxyphthalic acid in 50 ml of absolute tetrahydrofuran is combined within 15 minutes with 450 ml of a 0.3-molar borane-tetrahydrofuran complex solution in tetrahydrofuran and stirred for 16 hours at room temperature. Under ice cooling and under nitrogen, the mixture is carefully combined with water until cessation of hydrogen liberation, and then the mixture is concentrated and the residue triturated with ethyl acetate, vacuum-filtered, the mother liquor concentrated and purified on a silica gel column (system: dichloromethane/acetone 1+1). Yield: 5.5 g of 4-nitro-5-phenoxyphthalyl alcohol, mp 85°–86° C.-decomposition (from ethanol/water).

(e) 2.75 g of 4-nitro-5-phenoxyphthalyl alcohol in 60 ml of absolute tetrahydrofuran is stirred with 2.3 g of p-toluenesulfonyl chloride for one-half hour at room temperature, cooled to 0° C., and combined within 20 minutes with 720 mg of sodium hydride (80% strength). The mixture is stirred for 1 hour at 0° C. and for 3 hours at room temperature, concentrated, the residue dissolved in ethyl acetate/water, washed once with 1 N hydrochloric acid and three times with water, and concentrated. The crude product is purified on a silica gel column (system: cyclohexane/ethyl acetate 2+1). Yield: 1 g of 5-nitro-6-phenoxy-1,3-dihydroisobenzofuran, mp 77°–78.5° C. (from ethanol).

(f) 770 mg of 5-nitro-6-phenoxy-1,3-dihydrobenzofuran, 1 g of Raney nickel in 20 ml of ethanol are combined under boiling within 5 minutes with 0.3 ml of hydrazine hydrate and refluxed for 30 minutes, then vacuum-filtered, concentrated, and recrystallized from ethanol. Yield: 515 mg of 6-phenoxy-1,3-dihydroisobenzofuran-5-amine, mp 140°–143.5° C.

(g) As described in Example 1(g), 477 mg of 6-phenoxy-1,3-dihydroisobenzofuran-5-amine in 5 ml of pyridine is reacted with 0.24 ml of methanesulfonyl chloride.

Yield: 550 mg of N-(6-phenoxy-1,3-dihydroisobenzofuran-5-yl)methanesulfonamide, mp 159°–160° C.

EXAMPLE 8

(a) 23 g of 2-bromo-4,5-dimethylnitrobenzene and 28.6 g of 2,4-difluorophenol are reacted as disclosed in Example 7(b). Yield after distillation at 150° C. bath temperature and 1.5 mm Hg on a bulb tube and recrystallization from petroleum ether: 11.8 g of 2-(2,4-difluorophenoxy)-4,5-dimethylnitrobenzene, mp 82° C.

(b) 35 g of 2-(2,4-difluorophenoxy)-4,5-dimethylnitrobenzene in 190 ml of pyridine and 570 ml of water is oxidized as described in Example 7(c) with 328 g of potassium permanganate at 80°–90° C. and worked up. Yield: 31.8 g of 5-(2,4-difluorophenoxy)-4-nitrophthalic acid, mp 152.5°–155° C. (from ethanol/water).

(c) 3.36 g of 5-(2,4-difluorophenoxy)-4-nitrophthalic acid in 20 ml of absolute tetrahydrofuran is reduced as described in Example 7(d) with 150 ml of a 0.3-molar borane-tetrahydrofuran complex solution in tetrahydrofuran. After crystallization from ethanol/water and ethyl acetate/hexane, 2.1 g of 5-(2,4-difluorophenoxy)-4-nitrophthalyl alcohol is obtained, mp 123.5°–124.5° C.

(d) 2.8 g of 5-(2,4-difluorophenoxy)-4-nitrophthalyl alcohol is agitated with 45 ml of hydrobromic acid (48% strength) for 1 hour at 60° C., combined with water, the precipitate vacuum-filtered and recrystallized from ethanol. Yield: 3.2 g of 2-bromomethyl-5-(2,4-difluorophenoxy)-2-nitrobenzyl alcohol, mp 149°–150° C.

(e) 1.9 g of 2-bromomethyl-5-(2,4-difluorophenoxy)-4-nitrobenzyl alcohol in 40 ml of dichloromethane is combined with 1.7 g of tetrabutylammonium hydrogen sulfate. After 5 minutes, the mixture is combined with 5 ml of 1 N sodium hydroxide solution and after 15 minutes with 10 ml of 1 N sodium hydroxide solution and further agitated for 30 minutes. The dichloromethane phase is washed twice with water and twice with 1 N hydrochloric acid, dried, and concentrated.

The residue is purified on a silica gel column (system: cyclohexane/ethyl acetate 1+1) and recrystallized from diisopropyl ether. Yield: 785 mg of 6-(2,4-difluorophenoxy)-5-nitro-1,3-dihydroisobenzofuran, mp 105°–106° C.

(f) 970 mg of 6-(2,4-difluorophenoxy)-5-nitro-1,3-dihydroisobenzofuran in 80 ml of methanol is hydrogenated in the presence of 1 g of Raney nickel within 3 hours at 20 bar, filtered, concentrated, and recrystallized from ethanol. Yield: 770 mg of 6-(2,4-difluorophenoxy)-1,3-dihydroisobenzofuran-5-amine, mp 113.5°–114.5° C.

(g) 736 mg of 6-(2,4-difluorophenoxy)-1,3-dihydroisobenzofuran-5-amine in 8 ml of pyridine is reacted as described in Example 1(g) with 0.28 ml of methanesulfonyl chloride.

Yield: 750 mg of N-[6-(2,4-difluorophenoxy)-1,3-dihydroisobenzofuran-5-yl]methanesulfonamide, mp 176.5°–178.5° C.

EXAMPLE 9

(a) 7.2 g of 4-nitro-5-phenoxyphthalic acid in 60 ml of absolute tetrahydrofuran is combined under nitrogen within 30 minutes with 160 ml of a 0.3-molar borane-tetrahydrofuran complex solution in tetrahydrofuran and stirred for 16 hours at room temperature. Under ice cooling and under nitrogen, the mixture is combined with water, concentrated, dissolved three times in ethanol, and the solvent removed by distillation. The residue is dissolved in ethyl acetate and combined with 1.6 ml of sulfuric acid.

After 16 hours at room temperature, the mixture is washed three times with saturated sodium bicarbonate solution, and the organic phase is concentrated. The residue is purified on a silica gel column (system: cyclohexane/ethyl acetate 1+1). Yield: 1.2 g of 5-nitro-6-phenoxyphthalide, mp 132°–133° C. (from ethyl acetate) and 1.2 g of 6-nitro-5-phenoxyphthalide, mp 166.5°–167.5° C. (from ethanol).

(b) 950 mg of 5-nitro-6-phenoxyphthalide in 120 ml of methanol and 30 ml of tetrahydrofuran is hydrogenated in the presence of 2 g of Raney nickel within 3 hours at 20 bar, filtered, and concentrated. From methanol, 570 mg of 5-amino-6-phenoxyphthalide is obtained, mp 205°–206.5° C.

(c) As described in Example 1(g), 700 mg of 5-amino-6-phenoxyphthalide in 10 ml of pyridine is reacted with 0.3 ml of methanesulfonyl chloride.

Yield: 740 mg of N-(6-phenoxyphthalid-5-yl)methanesulfonamide, mp 153°–154° C. (from ethanol).

EXAMPLE 10

(a) As described in Example 9(a), 4.6 g of 5-(2,4-difluorophenoxy)-4-nitrophthalic acid in 20 ml of absolute tetrahydrofuran is reduced with 100 ml of a 0.3-molar borane-tetrahydrofuran complex solution in tetrahydrofuran and worked up. Crystallization from ethanol yields 1.3 g of 6-(2,4-difluorophenoxy)-5-nitrophthalide, mp 164°–165.5° C.

(b) 1.2 g of 6-(2,4-difluorophenoxy)-5-nitrophthalide in 120 ml of methanol and 30 ml of tetrahydrofuran is reduced as described in Example 9(b). Yield: 1 g of 5-amino-6-(2,4-difluorophenoxy)phthalide, mp 96°–98° C.

(c) 970 mg of 5-amino-6-(2,4-difluorophenoxy)phthalide in 10 ml of pyridine is reacted as disclosed in Example 1(g) with 0.32 ml of methanesulfonyl chloride.

Yield: 930 mg of N-[6-(2,4-difluorophenoxy)-phthalid-5-yl]methanesulfonamide, mp 155°–156.5° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzofuran derivative of the formula

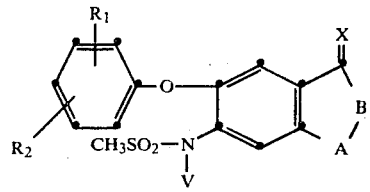

wherein

V is hydrogen or acetyl,

X is oxo or two hydrogen atoms, $R_1$ and $R_2$ each independently is hydrogen, fluorine, or chlorine, and —A—B— is —O—CH$_2$— or —CH$_2$—O—.

2. A benzofuran derivative of claim 1, wherein V is hydrogen.

3. A benzofuran derivative of claim 1, wherein $R_1$ is ortho-fluorine and $R_2$ is para-fluorine.

4. A benzofuran derivative of claim 1, 2 or 3, wherein —A—B— is —CH$_2$—O—.

5. N-(5-Phenoxy-2,3-dihydrobenzo[b]furan-6-yl)methanesulfonamide, a compound of claim 1.

6. N-[5-(2-Fluorophenoxy)-2,3-dihydrobenzo[b]furan-6-yl]methanesulfonamide, a compound of claim 1.

7. N-[5-(2,4-Difluorophenoxy)-2,3-dihydrobenzo[b]furan-6-yl]methanesulfonamide, a compound of claim 1.

8. N-[5-(2-Chloro-4-fluorophenoxy)-2,3-dihydrobenzo[b]furan-6-yl]methanesulfonamide, a compound of claim 1.

9. N-Acetyl-N-[5-(2,4-difluorophenoxy)-2,3-dihydrobenzo[b]furan-6-yl]methanesulfonamide, a compound of claim 1.

10. N-(3-Oxo-5-phenoxy-2,3-dihydrobenzo[b]furan-6-yl)methanesulfonamide, a compound of claim 1.

11. N-(6-Phenoxy-1,3-dihydroisobenzofuran-5-yl)methanesulfonamide, a compound of claim 1.

12. N-[6-(2,4-Difluorophenoxy)-1,3-dihydroisobenzofuran-5-yl]methanesulfonamide, a compound of claim 1.

13. N-(6-Phenoxyphthalid-5-yl)methanesulfonamide, a compound of claim 1.

14. N-[6-(2,4-Difluorophenoxy)phthalid-5-yl]methanesulfonamide, a compound of claim 1.

15. A pharmaceutical composition comprising an antiinflammatorily effective amount of a compound of claim 1 and a pharmaceutically acceptable adjuvant.

16. A pharmaceutical composition comprising an antiinflammatorily effective amount of two compounds of claim 1 and a pharmaceutically acceptable adjuvant.

17. A pharmaceutical composition of claim 15 or 16 wherein the amount of active ingredient is 1–250 mg and the amount of adjuvant is 50 mg–2 g.

18. A method of treating inflammation in a mammal comprising administering an antiinflammatorily effective amount of a compound of claim 1 to the mammal.

* * * * *